United States Patent [19]
Liboff et al.

[11] Patent Number: 5,441,495
[45] Date of Patent: Aug. 15, 1995

[54] ELECTROMAGNETIC TREATMENT THERAPY FOR STROKE VICTIM

[75] Inventors: Abraham R. Liboff, Birmingham, Mich.; Bruce R. McLeod, Bozeman, Mont.; Stephen D. Smith, Lexington, Ky.

[73] Assignee: Life Resonances, Inc., Bozeman, Mont.

[21] Appl. No.: 136,474

[22] Filed: Oct. 13, 1993

Related U.S. Application Data

[63] Continuation of Ser. No. 395,247, Aug. 17, 1989, abandoned.

[51] Int. Cl.⁶ ............................................. A61N 2/04
[52] U.S. Cl. ......................................... 600/9; 600/13
[58] Field of Search ................. 128/419 F, 421, 422, 128/424; 600/9, 13–15; 435/137

[56] References Cited

U.S. PATENT DOCUMENTS

| | | |
|---|---|---|
| 3,566,877 | 3/1971 | Smith et al. |
| 3,890,953 | 6/1975 | Kraus et al. |
| 3,893,462 | 7/1975 | Manning |
| 3,911,930 | 10/1975 | Hagfers et al. |
| 3,952,751 | 4/1976 | Yarger |
| 4,105,017 | 8/1978 | Ryaby et al. |
| 4,266,532 | 5/1981 | Ryaby et al. |
| 4,315,503 | 2/1982 | Ryaby et al. ............ 128/419 F |
| 4,428,366 | 1/1984 | Findl et al. |
| 4,459,988 | 7/1984 | Madurski |
| 4,535,775 | 8/1985 | Brighton et al. |
| 4,548,208 | 10/1985 | Niemi |
| 4,561,426 | 12/1985 | Stewart |
| 4,600,010 | 7/1986 | Dugot |
| 4,616,629 | 10/1986 | Meere |
| 4,622,952 | 11/1986 | Grodon |
| 4,622,953 | 11/1986 | Gordon |
| 4,654,574 | 3/1987 | Thaler |
| 4,683,873 | 8/1987 | Cadossi |
| 4,757,804 | 7/1988 | Griffith et al. |
| 4,932,951 | 6/1990 | Liboff et al. ............ 600/13 |
| 5,123,898 | 6/1992 | Liboff et al. |

FOREIGN PATENT DOCUMENTS 0144920  6/1985  European Pat. Off. ............ 600/13

OTHER PUBLICATIONS

NMR Imaging in Biomedicine, Mansfield et al., Apr. 13, 1982 pp. 297–310.
"Interactions Between Electro–Magnetic Fields and Cells," Chiabrera, et al., Plenum Publishing, 1985, pp. 281–291.
"A Role for the Magnetic Field in the Radiation–Induced Efflux of Calcium Ions from Brain Tissue in Vitro" Bio-electriomagnetics 6:327 337, 1985.
"Geomagnetic Cyclotron Resonance In Living Cells," Journal of Biological Physics, vol. 13, 1985.
"Clinical Experience With Low–Intensity Direct Current Stimulation of Bone Growth"; *Clinical Orthopedics and Related Research No. 124*, May 1977.

*Primary Examiner*—Lee S. Cohen
*Assistant Examiner*—Robert L. Nasser, Jr.
*Attorney, Agent, or Firm*—Dykema Gossett PLLC

[57] ABSTRACT

A method and apparatus for therapeutically treating stroke is provided. The apparatus includes a magnetic field generator for producing a controlled, fluctuating, directionally oriented magnetic field parallel to a predetermined axis projecting through the patient's cerebral tissue. In one aspect, a field detector measures the magnetic flux density along the predetermined axis. The applied magnetic field may comprise a full-wave rectified signal oscillated at predetermined frequencies to maintain a preselected ratio of frequency to the effective flux density, where the ratio maintains tissue viability and reduces edema by controlling ion electrolyte balance. This ratio is maintained by adjusting the frequency of the fluctuating magnetic field and/or by adjusting the intensity of the applied magnetic field after nulling out the local magnetic field at that region containing the target cerebral tissue.

15 Claims, 3 Drawing Sheets

ELECTROMAGNETIC TREATMENT THERAPY FOR STROKE VICTIM

This is a continuation of application(s) Ser. No. 07/395,247 filed on Aug. 17, 1989 now abandoned.

FIELD OF THE INVENTION

The present invention relates generally to methods and apparatus for the treatment of stroke victims and is aimed at alleviating post-stroke difficulties which often lead to death or disability. More specifically, the present invention discloses the use of magnetic fields for non-invasive treatment of stroke sequelae.

BACKGROUND OF THE INVENTION

In the United States, stroke-related illness is the third leading cause of death. Each year approximately 400,000 individuals in this country suffer a stroke. For those who survive, it is a major cause of long-term disability. Of every 100 persons surviving an acute stroke, it is estimated that only 10 are able to return to their previous activities without significant impairment. Forty percent of all individuals suffering an acute stroke episode are disabled to the extent that they require special assistance and, of these, ten percent need institutional care.

As will be appreciated by those skilled in the art, stroke is the interruption of normal blood flow in a region of the brain. This interruption of blood flow causes an oxygen deficit in the tissues of the brain which in turn produces unconsciousness and paralysis. Depending upon the severity of the oxygen deprivation, paralysis may be temporary or permanent. Stroke (or apoplexy) occurs most commonly as the result of a cerebral thromboembolism or cerebral hemorrhage and may also be caused by a cerebral embolism. Many strokes are linked to pre-existing conditions such as atherosclerosis, hypertension or an arterial aneurysm.

Cerebral function is primarily dependent upon an adequate supply of oxygen, glucose and other nutrients to the brain as provided by blood flow. In brain tissue, a high rate of glucose oxidation is necessary to meet the energy requirements of cellular ion pumps which maintain the sodium and potassium gradients across cell membranes. Because there is no significant storage of oxygen and glucose in cerebral tissue, neurons are dependent on adequate cerebral blood flow to deliver oxygen and glucose. When cerebral blood flow is interrupted, as in a stroke, tissue ischemia rapidly ensues. The neurons then become hypoxic. The effect of ischemia on the neuron is failure of the ion pumps which, as stated, are required to maintain ionic distribution across the membrane. There is a consequent rapid leakage of $K^+$ ions from within the cell to the extracellular volume. Carrier-mediated uptake of $Cl^-$ ions, resulting from elevated levels of $K^+$ ions and stimulated by $HCO_3^-$ ions, carries $Na^+$ ions and water into astrocytes. This initiates a vicious cycle whereby astroglial edema is increased which exacerbates tissue ischemia. The increasingly ischemic neurons then leak more $K^+$ ions into the extracellular space which further exacerbates the astroglial edema. The difficulties of post-stroke patient management are further complicated when blood flow is restored following a vascular accident due to a concomitant abrupt rise in water content in the tissue.

Various therapeutic measures have been used by others to treat the often fatal sequelae of stroke. In the final analysis, successful stroke therapy must be directed at preventing or minimizing the consequences of the initial acute circulatory failure and the resultant tissue ischemia. The target of such treatment is often the ischemic neuron or the cerebral ischemia edema that accompanies stroke. Glucocorticoid steroids, including dexamethasone and cortisone, have been administered in experimental trials, as well as agents that act as diuretics and/or inhibitors of anion transport. The latter have been useful in inhibiting the production of cerebrospinal fluid. Another therapeutic approach has been the use of barbiturates in anesthetic doses, which is presumed to relate to the associated depression of neuronal metabolic demands, allowing cells to better withstand cerebral ischemia. More specifically, the resulting decrease in the production of lactic acid and other acid metabolites tends to lessen secondary anoxic or vasogenic edema. The use of glycerol, naftidrofuryl and nimodopine to treat patients following acute ischemic stroke has also met with limited success.

A number of other therapeutic strategies for the treatment of stroke are under current investigation in the laboratory. One example is the proposed use of mild, whole-body hypothermia as a means of regulating the induction of heat shock proteins, which may play a role in protecting neural tissue from subsequent trauma in metabolic injury. Still another therapeutic approach involves the blockade of excitatory amino acid receptors which have been implicated in neuronal injury following prolonged anoxia. One such blocker is ketamine, dissociative general anesthetic. Other blockers include high concentrations of magnesium or antagonists of excitatory amino acids such as kynurenate or aminophosphonovalerate. It will be appreciated by those skilled in the art that conventional stroke therapies are only marginally successful.

In recent years, multi-disciplinary investigations of physiological processes have provided evidence suggesting that electric and magnetic fields play an important role in cell and tissue behavior. In U.S. Pat. No. 4,818,697, entitled *"Techniques for Enhancing the Permeability of Ions Through Membranes,"* which has been assigned to the assignee of the present invention and the disclosure of which is incorporated herein by reference, a method and apparatus are disclosed by which transmembrane movement of a preselected ion is magnetically regulated using a time-varying magnetic field. The fluctuating magnetic field is preferably tuned to the cyclotron resonance energy absorption frequency of the preselected ion. This important discovery brought to light the interplay of local magnetic fields and frequency dependence in ion transport mechanisms. It has now been discovered that by utilizing and extending the principles of cyclotron resonance tuning, unexpected and remarkable advances in the control and modification of physiological processes in living tissue can be achieved. In U.S. patent application Ser. No. 172,268, filed Mar. 23, 1988, the disclosure of which is incorporated herein by reference, the inventors of the present invention disclose that cyclotron resonance can be used to control tissue development. In U.S. patent application Ser. No. 254,438, entitled *"Method and Apparatus for Controlling the Growth of Non-Osseous, Non-Cartilaginous, Solid Connective Tissue,"* filed Oct. 6, 1988, the disclosure of which is incorporated herein by reference, the present inventors disclose a method of controlling the growth of non-osseous, non-cartilaginous connective tissue which utilizes cyclotron resonance frequencies. In U.S. patent application Ser. No. 295,164, entitled "*Techniques for Controlling Osteoporosis Using Non-Invasive Magnetic Fields,*" filed Jan. 9, 1989, the disclosure of which is incorporated herein by reference, the present inventors disclose a method of controlling osteoporosis using cyclotron resonance magnetic fields. In U.S. patent application Ser. No. 343,017, filed Apr. 25, 1989, entitled "*Methods and Apparatus for Regulating Transmembrane Ion Movement Utilizing Selective Harmonic Frequencies and Simultaneous Multiple ion Regulation,*" the disclosure of which is incorporated herein by reference, the present inventors disclose a method of utilizing therapeutic higher-harmonic frequencies and a method of simultaneously controlling multiple ions. These various inventions deal with the transport of specific ions across cell membranes.

The present invention discloses a new and unique apparatus and non-invasive treatment therapy for stroke victims which is directed at relieving post-stroke difficulties that often lead to death or disability. This new treatment therapy may be used to supplement or replace conventional therapeutic modalities that employ a variety of pharmacologic agents.

SUMMARY OF THE INVENTION

In one aspect, the present invention provides an apparatus for alleviating post-stroke sequelae, including ion imbalance and tissue ischemia, which includes means for generating an applied magnetic flux parallel to a predetermined axis and projecting through a predetermined space. The predetermined space is occupied by cerebral tissue of a living subject, either man or animal, wherein the tissue has been damaged during a stroke. Means for measuring magnetic flux density parallel to the predetermined axis extending through the predetermined space is provided so that the magnetic flux density along the axis can be monitored. Means in association with the flux generating means is provided so that the applied magnetic flux can be oscillated. Finally, means for creating and maintaining a relationship between the rate of fluctuation of the magnetic flux and the intensity of the magnetic flux density is provided, where the predetermined relationship alleviates post-stroke sequelae in the cerebral tissue.

In one embodiment, the means for applying a magnetic flux includes two opposed field coils arranged in Helmholtz configuration such that an applied magnetic field having known parameters along the predetermined axis can be generated between the coils. In another embodiment, a second pair of field coils are placed such that they generate an applied magnetic flux along an axis perpendicular to the predetermined axis defined by the first coil pair. In this same manner, a third pair of opposed coils can be utilized such that magnetic fields are applied by the three coil pairs along the x, y, z axes of a Cartesian coordinate system. The second and third coil pairs are similarly actuated to provide a predetermined relationship between the frequency of the magnetic flux and the intensity of the magnetic flux density.

In another aspect, a method for alleviating post-stroke sequelae is provided utilizing the apparatus of the present invention. Therein, a region of cerebral tissue of a living subject, either man or animal, which has been damaged during a stroke is positioned adjacent a magnetic field generating means. A magnetic flux extending through the space in which the cerebral tissue is positioned is generated parallel to a predetermined axis projecting through the tissue. A relationship is then created between the frequency of the oscillating magnetic flux and the intensity of the magnetic flux density where the relationship alleviates post-stroke sequelae in the cerebral tissue. In a preferred embodiment of the present invention, the magnetic flux generating means comprises a pair of field coils as previously described. Also, in a preferred embodiment of the invention, the predetermined therapeutic relationship between the frequency of the magnetic flux permeating the cerebral tissue and the intensity of the magnetic flux is determined by the cyclotron resonance equation $f_c/B = q/(2\pi m)$, where $f_c$ is the frequency in Hertz, B is the average value of the magnetic flux density in Tesla parallel to the predetermined axis, $q/m$ has a value of from about $5 \times 10^5$ to about $100 \times 10^6$ Coulombs per kilogram and where B has a value of less than about $1 \times 10^{-2}$ Tesla. In a particularly preferred embodiment, $q/m$ is the charge-to-mass ratio of a preselected ion present in the cerebral tissue.

In still another aspect, a system for alleviating post-stroke sequelae is provided which includes means for generating an applied magnetic flux parallel to a predetermined axis and projecting through a predetermined space where the space is occupied by post-stroke cerebral tissue of a living subject. In this particular configuration, the magnetic flux generating means includes at least two opposed field coils having an axis extending therethrough and parallel to the predetermined axis projecting through the predetermined space. Each of the field coils has at least two windings. One winding is designated an ac winding and the other is designated a dc winding. Means in association with the coils is provided for supplying a direct current to the dc winding and an alternating current to the ac winding. Means for measuring the ambient or local field existing in the predetermined space in the region of the cerebral tissue is also provided. Means in association with the flux generating means for controlling the direct current to the dc windings is supplied such that the dc windings may be activated to create a magnetic flux which reduces the ambient magnetic flux to substantially zero. A full-wave rectifier circuit and an oscillator are provided in association with the ac windings and the current supply means in order to produce an ac magnetic field component along the predetermined axis in the predetermined space which has a preselected rms value, where the rms value alleviates post-stroke sequelae in the cerebral tissue. In a thoroughly equivalent manner, the system may use a sinusoidal signal to the ac windings, offset by a constant bias current equal to the rms-value utilized when full-wave rectification is used.

The system may further include a second pair of opposed field coils which define an axis extending through the cerebral tissue which is perpendicular to the predetermined axis defined by the first coil pair. Further, a third coil pair can be provided such that the ambient field along the x, y, z axes of a Cartesian coordinate system is reduced to zero, with an applied field having the therapeutic non-zero average value as provided by the present invention being generated along each of the axes.

With respect to the aforementioned system which includes ac windings and dc windings, there is provided by the present invention a method for alleviating post-stroke sequelae which comprises the steps of generating an applied magnetic flux parallel to a predetermined axis which projects through a predetermined space, with the space being occupied by cerebral tissue of a living subject which has been damaged by the effects of a stroke. The ambient field along the predetermined axis in the predetermined space is measured using a magnetic field sensor. Utilizing the dc windings and a power supply, a magnetic flux is generated which reduces the ambient field to substantially zero along the axis. The ac windings are then used to generate an ac magnetic field having a component along the predetermined axis which has a non-zero average value that is effective in alleviating post-stroke sequelae in the cerebral tissue.

Alleviating stroke sequelae through the use of higher-harmonic tuning and multiple ion tuning is also provided.

DESCRIPTION OF THE PREFERRED EMBODIMENTS OF THE INVENTION

Figures 1, 2:
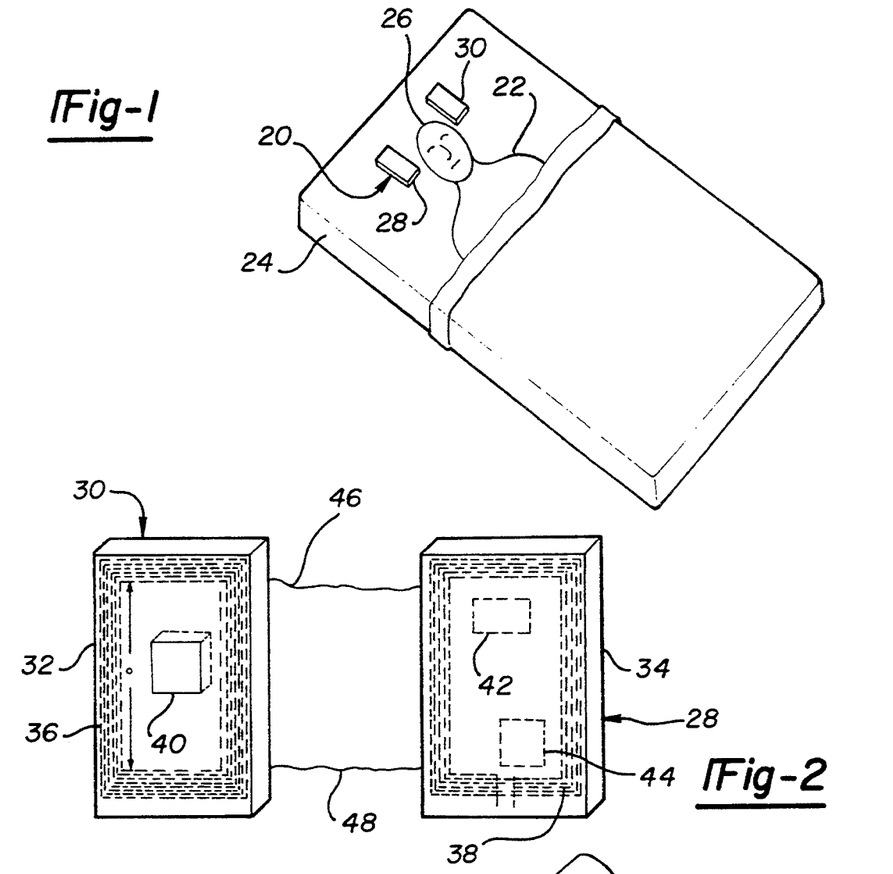
FIG. 1 diagrammatically illustrates one preferred placement of the apparatus of the present invention.
FIG. 2 is a front elevational view of the treatment heads of the present invention in one embodiment.

Referring now to FIG. 1 of the drawings, stroke treatment apparatus 20 is shown in position on patient 22 in hospital bed 24. It is to be understood that both the apparatus and the method of the present invention are suitable for use in alleviating post-stroke sequelae in both animal and human subjects. Thus, the target tissue which is to be affected is a region of living cerebral tissue in a subject which has been damaged by oxygen deprivation as the result of a stroke. As used herein, the term "stroke" and "sequelas" shall have their customary meanings with reference to the discussion of these matters in the foregoing background of the invention. In particular, "sequelas" shall include localized ion imbalance and cerebral tissue ischemia.

The patient's cranium 26 is positioned in a predetermined volume between treatment heads 28 and 30 of stroke treatment apparatus 20. It is within this predetermined space or volume that the therapeutic oscillating magnetic field is generated. Hence, as will be appreciated, there exists within cranium 26 cerebral tissue which has been damaged by the effects of a recent stroke. Since it is believed that one of the primary benefits of the present invention relates to the prevention or reduction of the ion imbalance which occurs as the result of neuronal ischemia, which in turn leads to astroglial edema, it is preferred that treatment be commenced as soon as possible following the occurrence of the stroke.

In order to better appreciate the configuration of coils 28 and 30 as provided by the present invention, reference is now made to FIG. 2 of the drawings in which treatment heads 28 and 30 are shown as including housings 32 and 34 of a non-magnetic material such as plastic. Each housing 32, 34 encloses a field coil 36 and 38. At least one of the treatment heads encloses a magnetic field sensing device 40, such as a Hall-effect device, shown in FIG. 2 enclosed within housing 32 of treatment head 30. The power source for driving the field coils is preferably external, but may be a battery or the like shown as power source 42 in treatment head 28.

While field coils 36 and 38 are the preferred means by which an applied magnetic field is generating in the present invention, those skilled in the art will appreciate that other electromagnets or possibly permanent magnets may be adapted for use in the present invention, and any such use is intended to come within the scope of the present invention. Also, the radius of each field coil 36 and 38, as well as the turns of the windings, may vary in accordance with the principles of the present invention. In the most preferred arrangement, the geometry and relative position of treatment heads 28 and 30 during treatment are such that field coils 36 and 38 operate as Helmholtz coils. Hence, those skilled in the art will recognize that in the most preferred arrangement, field coils 36 and 38 are substantially identical, field-aiding, parallel coaxial coils separated by a distance equal to the radius of each coil.

It will be appreciated that the cerebral tissue to be affected will generally be subject to local magnetic influences. As used herein, the term "local magnetic field," "ambient magnetic field" or the like shall be defined as the magnetic influences, including the earth's magnetic field or geomagnetic field, which create a local magnetic flux that flows through the target tissue. "Magnetic flux density" shall be defined in the customary manner as the number of magnetic field lines per unit area through a section perpendicular to the direction of flux. Factors contributing to the local magnetic field in addition to the geomagnetic field may include localized regions of ferromagnetic materials or the like. In one embodiment of the present invention, field coils 36 and 38 are used to create an applied, fluctuating magnetic field which, when combined with the local magnetic field parallel to a predetermined axis extending longitudinally between coils 28 and 30., produces a combined magnetic field or composite field having a component along the axis which has a precisely controlled, predetermined ratio of frequency to average magnetic flux density.

Figure 3:
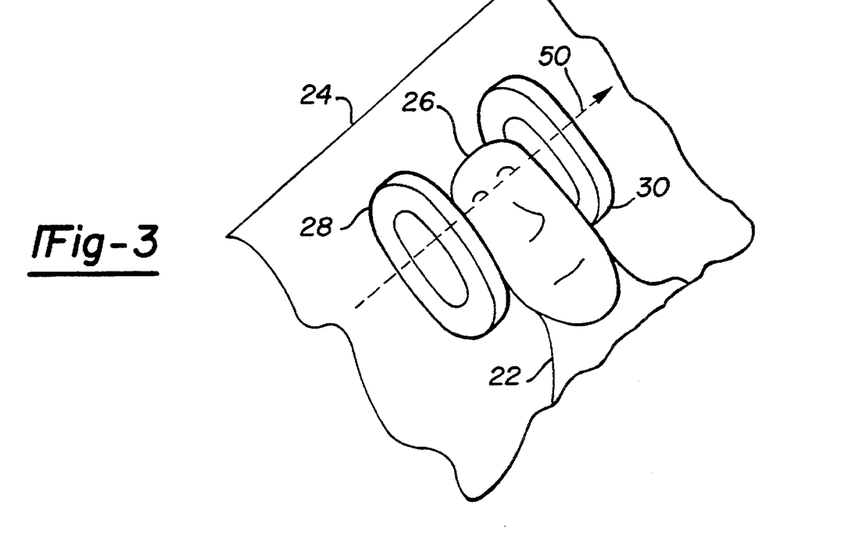
FIG. 3 illustrates the placement of the apparatus of the present invention with respect to a predetermined axis.

In one embodiment, and referring again to FIG. 2 of the drawings, this relationship is created using microprocessor 44 which is in communication with electronics necessary to control the oscillation and intensity of the magnetic flux which permeates the target cerebral tissue. Also, leads 46 and 48 are shown by which the various components of stroke treatment apparatus 20 are interconnected, along with other such leads which are not shown. Magnetic sensor or magnetometer 40 measures the total or composite magnetic flux which passes through the predetermined space between treatment heads 28 and 30 and thus provides an accurate measurement of the magnetic field which permeates the cerebral tissue of patient 22 within cranium 26. Predetermined axis 50 is shown in FIG. 3 as extending between treatment heads 28 and 30. In FIG. 3, treatment heads 28 and 30 are shown in a slightly different configuration than that depicted in FIGS. 1 and 2 to emphasize the nature of field coil action. It will be appreciated that the applied field generated using treatment heads 28 and 30 may be in either direction of predetermined axis 50 and that the local or ambient magnetic field will also have a component along axis 50 which either augments or decreases the applied magnetic flux. The relatively low applied flux density in the precise, predetermined relationships of combined flux density and frequency provided by the present invention are to be maintained during treatment, notwithstanding the influence of the local magnetic field. This may achieved in essentially two preferred manners which will be explained more fully herein. Thus, magnetic field sensor 40 is provided to determine the level of the magnetic flux density of the local magnetic field.

Figure 4:
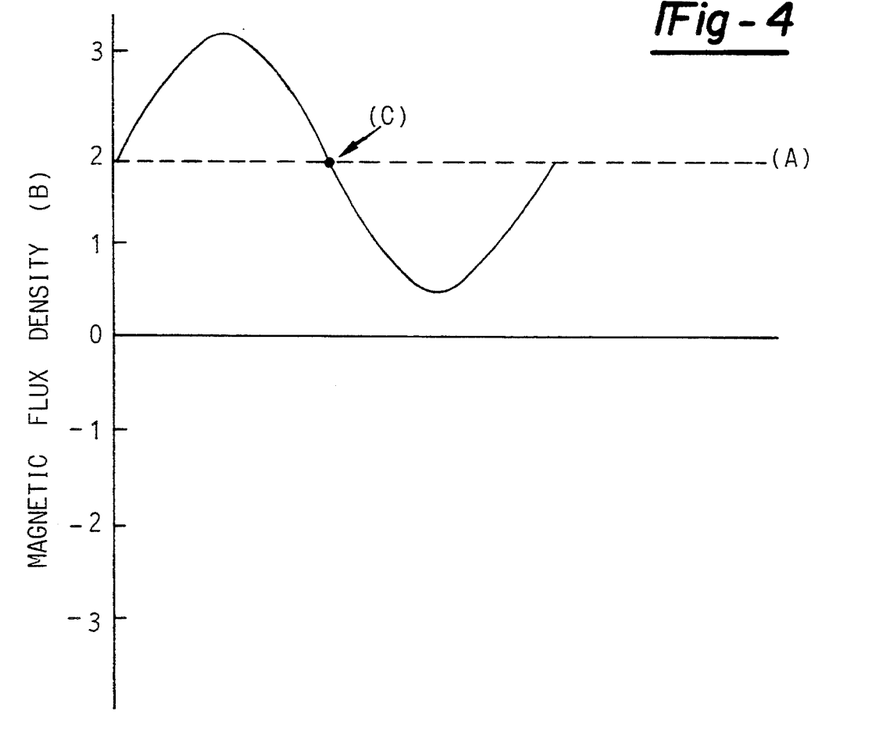
FIG. 4 is a graph which illustrates the value (B) in the present invention.

The unexpected and superior results of the present invention are achieved by creating a fluctuating magnetic field having a magnetic flux density parallel to predetermined axis 50, with the magnetic flux density along axis 50 being maintained at a predetermined ratio of the frequency of the fluctuations to the non-zero value of the magnetic flux density. In this embodiment, the magnetic flux density parallel to predetermined axis 50 has a non-zero average value. More specifically, as illustrated in FIG. 4 of the drawings, the therapeutic magnetic field of the present invention can be thought of as a static field having reference level A on which a fluctuating magnetic field is superimposed. It comprises an ac component which varies in amplitude but not direction and a dc reference around which the ac component varies. Reference level A is the non-zero average value of the flux density (B). Therefore, it will be understood that the non-zero average, or net average value where the magnetic field is the combination of the local field and the applied field, along predetermined axis 50 is utilized since the magnitude B of the composite flux density changes at a predetermined rate due to oscillation or fluctuation of the applied magnetic flux. Thus, an average value is utilized which is a non-zero average value illustrated at point (c). This reflects that although the magnetic flux density along the axis is oscillating at a controlled rate, the field is regulated to ensure that the field is always unipolar; that is, the field is always in the same direction along predetermined axis 50.

As stated, it has been found that rather precise relationships of the flux density of the magnetic field to the frequency of the fluctuations are used in the present invention to provide therapeutic results. These ratios of frequency to composite flux density are found in accordance with the following equation:

$$f_c/B = q/(2\pi m)$$

where $f_c$ is the frequency of the combined magnetic field in Hertz, B is the net average value of the magnetic flux density of the magnetic field (the combined field where a local field component is present) parallel to predetermined axis 50 in Tesla and q/m has a value of from about $5 \times 10^5$ to about $100 \times 10^6$ Coulombs per kilogram. B perferably has a value not in excess of about $1 \times 10^{-2}$ Tesla. In order to alleviate post-stroke sequelae, the following frequency and associated combined magnetic flux density (B) are preferred:

| fc (Hertz | B (Tesla) |
| --- | --- |
| 16.0 | $12.68 \times 10^{-6}$ | at an ac amplitude, peak-to-peak of 40 microTesla.

In use, the cerebral tissue is then subjected to a fluctuating magnetic field as described herein for a period of time effective to alleviate post-stroke sequelae of the tissue. While the length of time necessary for successful treatment may vary, it is anticipated that up to about 100 days of treatment will provide beneficial results. Longer treatment may be desirable in certain applications.

In another embodiment of the present invention, values for q and m are determined with reference to a preselected ionic species. It will be known by those skilled in the art that the biochemical milieu of cerebral tissue comprises a mixture of various ions in the intracellular and intercellular fluids and that, as stated, ion imbalance due to neuron ischemia contributes to the cycle of further tissue damage. These ions include potassium ions, magnesium ions, sodium ions, chloride ions, phosphate ions, sulfate ions, carbonate ions, bicarbonate ions and the like and various ions formed by the dissociation of amino acids, proteins, sugars, nucleotides and enzymes. By utilizing the values of charge and mass for a preselected ion in the equation set forth above, which will be recognized by those skilled in the art as the cyclotron resonance relationship solved for $f_c/B$, ratios of frequency to magnetic flux density can be determined which will alleviate post-stroke sequelae in accordance with the present invention. By using the charge-to-mass ratio of a preselected ion, a specific cyclotron resonance frequency for the ion can be determined. By then tuning stroke treatment apparatus 20 to maintain a combined magnetic flux density having the proper cyclotron resonance frequency, cerebral tissue containing the preselected ion can be treated to bring about the desired alleviation of post-stroke sequelae. More specifically, by tuning to $K^+$ it is believed that potassium leakage from ischemic neurons can be slowed or reversed.

It will also now be appreciated by the prior explanation of preferred embodiments of the present invention and from the equation for establishing a cyclotron resonance relationship, that either the frequency of the fluctuating magnetic field or the magnitude or intensity of the magnetic flux density along the predetermined axis, or both the frequency and the intensity of the flux density, can be adjusted to provide a magnetic field which has the desired characteristics. However, it is preferred to maintain a constant frequency which thus requires that the intensity of the applied magnetic flux density be adjusted to compensate for changes in the local magnetic field in order to maintain a constant ratio of frequency to magnetic flux density. For example, if it is necessary to maintain a frequency of 16 Hz and an average flux density of $4.07 \times 10^{-5}$ Tesla for $K^+$, changes in the local field which would otherwise cause unwanted deviations in the combined magnetic flux density must be corrected by increasing or decreasing the applied magnetic flux density accordingly. This is most preferably performed by the microcontroller in connection with both the field generating means and the field-sensing device. Alternatively, if changes in the combined magnetic flux density occur due to changes in the local magnetic field, the frequency of the oscillations can then be changed so that the preferred therapeutic ratio is maintained. Once again, it is important to realize that the value of B is the average composite magnetic flux density parallel to the predetermined axis since the magnitude of the flux density changes as the field is oscillated. It will be understood that detection of changes in the magnetic field due to changes in the ambient component should be at intervals frequent enough to provide a frequency-to-magnetic field ratio which is substantially constant, notwithstanding the changes in the local field component.

Referring again to FIG. 2 of the drawings, each field coil 36, 38 preferably has up to about 3000 turns or loops of conducting wire, the diameter d of each loop being preferably up to about 300 centimeters. The number of turns of wire n, the diameter of the coils, the separation of the coils, and the wire gauge are critical only insofar as conventional practice requires constraints on these and other design parameters to allow optimal performance characteristics in achieving predetermined flux densities as required in the preferred practice of the present invention. As stated, other magnetic field generating means may be suitable for use in the present invention and are contemplated as falling within the scope of this invention.

It is also to be understood that the applied magnetic field which results in a combined magnetic flux density along predetermined axis 50 may be produced by a sinusoidal signal or from a full-wave rectified signal applied to field coils 36, 38. It may also be appropriate in some instances to reduce components of the local magnetic field which are not parallel to predetermined axis 50 to zero through the use of additional coils positioned at right angles to coils 28 and 30 to create an opposite but equal field. It may also be suitable to reduce the local magnetic field component to zero throughout treatment using additional coils or the like.

Figure 5:
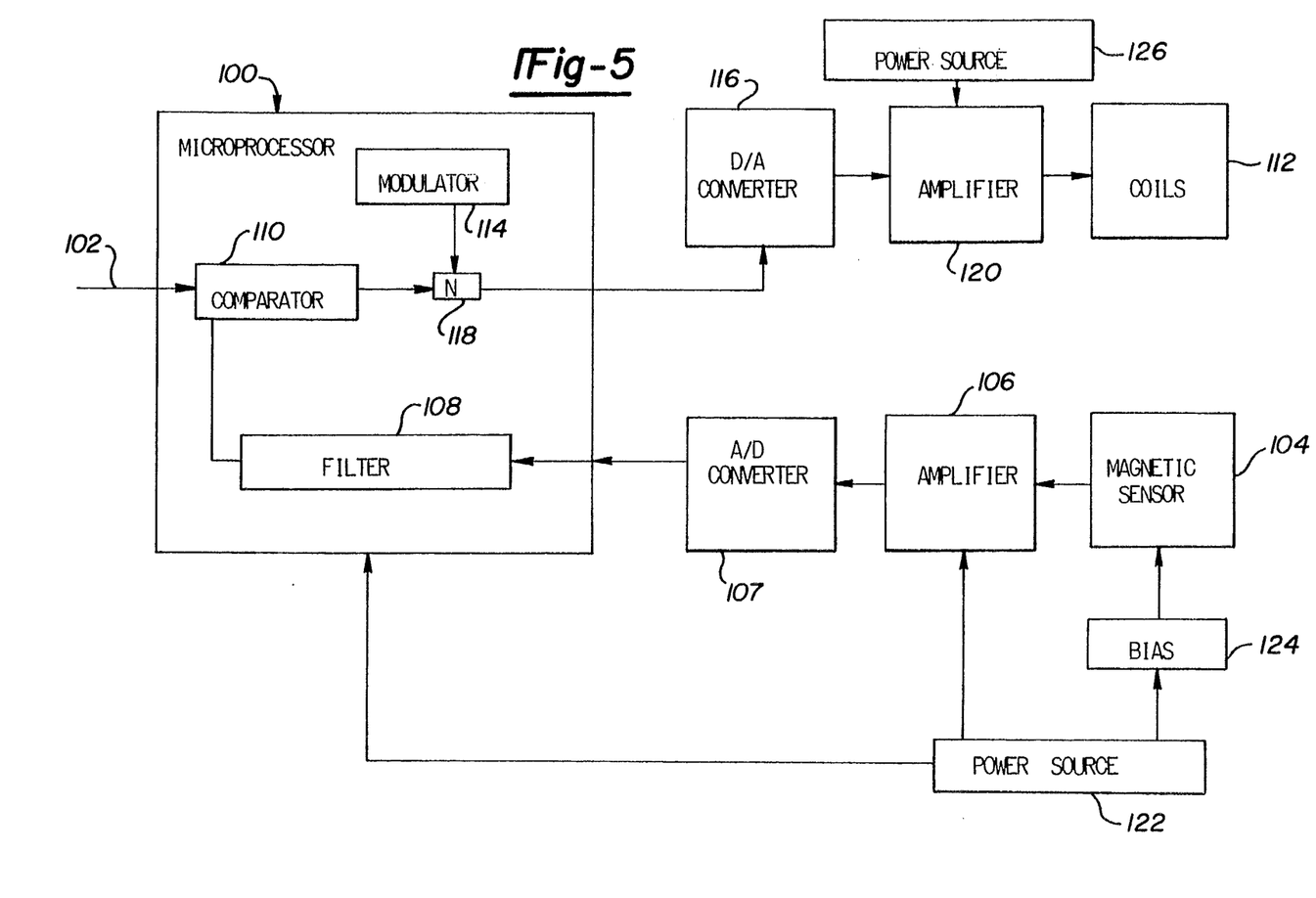
FIG. 5 is a block diagram of the functional elements of a preferred circuit for use in the present invention.

Referring now to FIG. 5 of the drawings, a block diagram is shown which depicts one preferred arrangement of the circuits of stroke treatment apparatus 20 in functional segments. Numerous other circuit arrangements may be possible if the principles of the present invention are faithfully observed. Microcontroller or microprocessor 100 is seen by which the composite magnetic field is maintained at a constant predetermined level despite changes in the ambient component as previously described. In this respect, input 102 is provided by which a set point value of the predetermined composite magnetic flux density along a predetermined is through the target tissue is input into microprocessor 100. As will be shown, the composite field strength is compared to this set point value to generate an error equal to the difference in the set point value and the measured value of the composite magnetic flux density along the axis.

Magnetic field sensor 104 is provided by which the magnitude of the composite field which passes through the target tissue along the axis is measured. It is preferred that magnetic field sensor 104 comprise a Hall-effect device which, as will be known by those skilled in the art, produces an analog signal. The magnetic field sensor 104 constantly monitors the composite magnetic field, sending a signal to microprocessor 100. It will be understood that the output of a Hall-effect magnetic sensor is relatively small; thus, magnetic field sensor amplifier 106 is provided by which the signal from magnetic field sensor 104 is amplified, for example, up to three thousand times its original value. Since a Hall-effect device produces an analog signal, analog-to-digital converter 107 is provided by which the amplified signal from magnetic field sensor 104 is converted to a digital signal which can be used by microprocessor 100. It is preferred that the analog-to-digital converter be provided on-board the microprocessor chip.

As will be appreciated, the amplification of the magnetic field sensor signal may produce an unwanted noise level. Also, sudden changes in the magnetic field intensity may occur which make it difficult to determine the true average value of the composite magnetic flux density. Hence, the signal from analog-to-digital converter 106 which is input into microprocessor 100 is filtered by software filter 108 to remove shot noise and sudden fluctuations in the composite field detected by magnetic field sensor 104. Although it is preferred that filter 108 comprise software in microprocessor 100, a discrete filter could be used. In this embodiment, software filter 108 is a digital filter, preferably an integrator with a time constant of approximately 0.5 seconds. In other words, the changes in the magnitude of the composite magnetic field which are compensated for by increasing or decreasing the applied field are long-term changes of 0.5 seconds or more. Hence, the time constant of filter 108 should be such that momentary fluctuations are filtered out.

Microprocessor 100 includes logic which calculates the non-zero net average value of the composite magnetic flux density. This non-zero average value is then compared at a comparator 110 in microprocessor 100 to the predetermined dc reference or offset value which is input into microprocessor 100 via input 102. It should be noted that this reference value is preferably established by dedicated circuitry in microprocessor 100, although variable input means could be included by which the set point value could be changed. An error statement is then generated defining the difference in the measured value of the composite magnetic flux density and the set point or reference value. Microprocessor 100 then determines the magnitude of the output necessary to drive magnetic field generating coils 112 to bring the composite magnetic flux density back to the set point.

Software field modulator or oscillator 114 is provided by which an ac or fluctuating component is superimposed on the digital output signal which is input into digital-to-analog converter 116. From the previous discussion of the present invention, it will be understood that software field modulator 114 of microprocessor 100 in the preferred embodiment of the present invention is preset to a fixed, predetermined frequency to produce the desired predetermined ratio of frequency-to-magnetic flux density value. In another embodiment, the feedback system of the present invention is such that changes in the composite magnetic flux density are measured, whereupon microprocessor 100 determines the necessary change in frequency to maintain the predetermined relationship. In that embodiment, software field analog converter 116 be provided on-board the microprocessor chip. Hence, software field modulator 114 provides the ac component at node 118.

The signal from digital-to-analog converter 116 is fed to voltage-to-current amplifier 120, the output of which drives magnetic field generating coils 1.12 in the desired manner. Hence, the composite field is held substantially constant despite changes in the ambient component.

While several arrangements of power sources are suitable, it is preferred that power supply 122 be provided to power magnetic field sensor amplifier 106, microprocessor 100 and magnetic field sensor 104, the latter via bias circuitry 124. A separate power source 126 is preferred for voltage to current amplifier 120.

Having fully described the apparatus of the present invention, including its manner of construction, operation and use, the method of the present invention will now be described. It is to be understood that this description of the method incorporates the foregoing discussion of the novel apparatus. In this aspect, the present invention provides a method of alleviating post-stroke sequelae in man or animals. This is achieved in one embodiment by generating a fluctuating, directionally-oriented magnetic field which projects through the target cerebral tissue. The magnetic field generating means preferred for use is previously described. The magnetic field so generated has a magnetic flux density of precisely controlled parameters which passes through the target cerebral tissue parallel to a predetermined axis projecting through the tissue. As will be known by those skilled in the art and as has been clearly explained, the local magnetic field to which the target tissue is subjected will have a component which is parallel to the predetermined axis and which thus aids or opposes the applied or generated magnetic field along the axis. At times, the local component may be zero. In the method of the present invention, the density of this combined magnetic flux, and more specifically the net average non-zero value of the combined magnetic flux density, is controlled to provide a precise relationship between the flux density along the axis and the frequency of the applied magnetic field which is oscillating at a predetermined value. Most preferably this is accomplished by adjusting the intensity of the applied field to compensate for changes in the local field. Thus, in one embodiment, the present invention provides a method of treating post-stroke cerebral tissue by creating a magnetic field which penetrates the tissue and which has a predetermined relationship between frequency of oscillation and average flux density. In the most preferred embodiment, the predetermined relationship or ratio of frequency-to-field intensity is determined with reference to the equation:

$$f_c/B = q/(2\pi m)$$

where $f_c$ is the frequency of the combined magnetic field along the predetermined axis in Hertz, B is the non-zero net average value of the magnetic flux density of the combined magnetic field parallel to the axis in Tesla and q/m is in Coulombs per kilogram and has a value of from about $5 \times 10^5$ to about $100 \times 10^6$. B preferably has a value not in excess of about $1 \times 10^{-2}$ Tesla.

In order to maintain a fluctuating magnetic field having the desired parameters, it may be necessary to monitor changes in the composite magnetic field parallel to the predetermined axis. As stated, this is preferably carried out with a Hall-effect device or the like which produces an analog signal. This analog signal is periodically sampled by microprocessing means which then calculates the necessary frequency and/or magnitude of the applied magnetic field to maintain the preprogrammed, predetermined ratio previously described. Of course, it will now be understood that it is the combined magnetic flux which is sensed by the magnetic field sensor. The magnetic field generating means is used to adjust the magnitude of this composite field where appropriate.

In one embodiment, the method includes controlling the average value of the applied magnetic flux density along a predetermined axis to maintain a predetermined ratio of frequency-to-composite magnetic flux density. In another embodiment, the frequency of the fluctuations is adjusted to maintain this relationship in which changes in the combined magnetic flux density due to changes in the local magnetic field are detected. Moreover, a combination of these two methods may be used wherein both the frequency and the magnitude of the magnetic field flux density are adjusted to maintain the predetermined relationship of the present invention.

Hence, the method of the present invention includes the steps of creating and maintaining a predetermined relationship between the frequency of a fluctuating magnetic field and the flux density of the field. In particularly preferred embodiments, a frequency of 16 Hertz and an average flux density of $2.09 \times 10^{-5}$ Tesla are utilized. This combination of frequency and flux density is particularly useful in alleviating post-stroke sequelae. Another preferred frequency which is useful is 16 Hertz and $1.27 \times 10^{-5}$ Tesla.

In a preferred embodiment of the method of the present invention, the ratio of frequency-to-flux density is determined by selecting a preselected ion present in the target cerebral tissue and tuning the fluctuating composite magnetic flux density to the specific cyclotron resonance frequency for the ion. The preferred ions for alleviating post-stroke sequelae are $Li^+$, $K^+$, $Mg^{++}$, and $Ca^{++}$. Tuning to other ions may also provide beneficial results.

Finally, the subject cerebral tissue is exposed to the therapeutic magnetic flux in accordance with the present invention for a period of time sufficient to help alleviate post-stroke sequelae, including astroglial edema. It is believed that exposure in accordance with the present invention for about 100 hours will produce some beneficial results.

It is also to be understood that although the present invention has been described in connection with the small coils illustrated in the drawings, larger coils placed at the ends or sides of hospital bed 24 may be utilized and that provision may be made for adjusting these coils relative to the subject's head. Hence, it is contemplated that the axis of this coil system can be oriented either transverse or parallel to the body axis. In the transverse orientation, the axis may be set along the lateral direction, along the anterior-posterior direction, or at any angle between these extremes.

In another preferred embodiment of the present invention, treatment heads 28 and 30 of stroke treatment apparatus 20 contain two discrete but otherwise equal windings. Each head contains a dc winding and an ac winding. These windings are closely wound, either as alternate wires, as alternate layers, or in adjacent planes. Those skilled in the art will recognize that the closeness of the winding arrangement will ensure that the two separate magnetic fields generated at a point distant from the two windings (when each carries substantially the same current) will be substantially the same. The dc winding in one coil is connected in series, aiding So the dc winding in the other coil. The ac winding in one coil is similarly connected in series, aiding to the ac winding in the other coil.

The pair of dc windings are energized by a dc power supply that provides a current which reduces the component of the local or ambient field along the axis of the coil pair at the desired treatment region to a value that is substantially zero. Again, the ambient field is measured by magnetic field sensing means such as a fluxgate magnetometer or the like. The ac windings, in this embodiment, are preferably energized by a full-wave rectifier circuit providing a current which produces a resulting ac magnetic field component along the coil axis at the desired treatment region that varies in time at the therapeutic frequency. The rms current of the rectified signal in the ac coil pair is adjusted until a preselected rms magnetic field component at the treatment region is achieved. It will be understood that once the ambient field is measured, knowledge of the coil geometry and number of turns will allow a predetermined calibration, enabling the operator to automatically achieve the required ambient field hulling current as well as the rms current necessary to create the preselected rms magnetic field.

In this embodiment utilizing a rectified signal in the ac windings, the frequency of the fluctuating magnetic field is set at a predetermined value, and the effective or root-mean-square value of the applied magnetic flux density is then regulated to produce a ratio of frequency to rms that acts to suppress edema and assist in the alleviation of post-stroke sequelae. Preferred ratios of frequency-to-field intensity are determined with reference to the equation:

$$\frac{f_0}{B_0} = q/2\pi m$$

where $f_O$ is the frequency of the fluctuating magnetic field in Hertz, $B_0$ is the non-zero rms value of the magnetic field component winding along the coil axis in Tesla, $(q/m)$ is in Coulombs per kilogram and has a value of from about $5 \times 10^5$ to about $100 \times 10^6$. $B_O$ preferably has a value not in excess of $1 \times 10^{-2}$ Tesla. In one embodiment, the values of q and m are selected with reference to the charge and mass of a preselected ion. Other relationships between frequency and magnitude may be useful or even desirable in a particular application.

In another embodiment, a sinusoidal current is employed in the ac windings with a direct current offset resulting in a non-zero average magnetic field to achieve the required magnetic field along the predetermined axis that is therapeutically effective.

Figure 6:
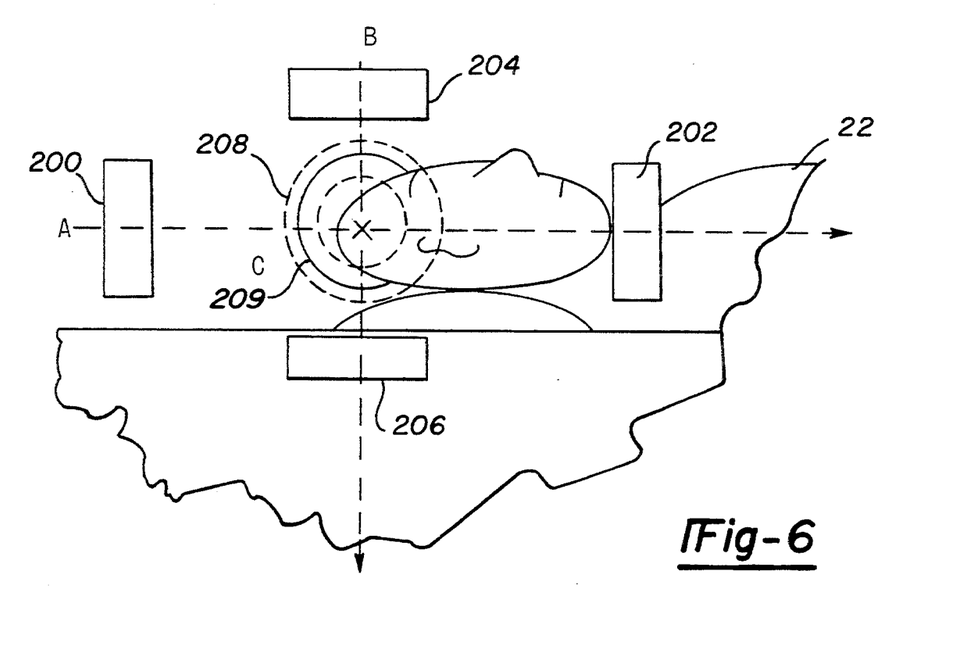
FIG. 6 is a side elevational view in which the present invention is shown utilizing three pairs of coils along x, y, and z axes.

In still another embodiment, and referring now to FIG. 6 of the drawings, three pairs of Helmholtz-like coils generate applied magnetic fields along the x, y and z axes of a Cartesian coordinate system. Coil pair A comprises treatment heads 200 and 202, with treatment head 202 being showed as a collar-like coil. Coil pair B comprises treatment heads 204 and 206, and coil pair C similarly comprises a pair of opposed coils, one of which is shown in phantom as treatment head 208 and the other as treatment head 209. It will be appreciated that these coils may comprise single windings or may be provided in the combination ac and dc windings as previously described. Also, it is preferred that each pair be provided with a magnetic field sensing device in order to measure the magnetic field component along each respective axis, a, b, and c, the latter being shown by an "x" extending into the plane of the drawing. In other words, the axes of the three coil pairs will be mutually perpendicular, intersecting at the desired treatment region in the patient's head. The therapeutic frequency is generated by each coil pair in the aforementioned described manner. Where the coil pairs include ac and dc windings, the ambient field component along each axis is reduced to substantially zero.

In still another embodiment of the present invention, post-stroke sequelae are alleviated by creating and maintaining a predetermined relationship between the frequency of the fluctuations and the non-zero average value of the magnetic flux density along the predetermined axis based on the charge-to-mass ratio of the preselected ion, wherein this predetermined relationship is determined using the equation $f_{ch} = XBq/2\pi m$. Accordingly, $f_{ch}$ is the frequency of the fluctuating magnetic flux density in Hertz, B is the non-zero average value of the flux density parallel to the predetermined axis in Tesla, q is the charge of the preselected ion in Coulombs, m is the mass of the preselected ion in kilograms, and X is a preselected odd integer greater than one. In this manner, a number of higher harmonic frequencies are provided by which therapeutic results may be achieved.

It will be recognized that the fundamental therapeutic frequency $f_c$ is effectively multiplied by a selected odd integer to produce a frequency which also causes the desired therapeutic result. Unless otherwise specified, as used herein, the term "odd integers" or "odd integer" shall mean positive, non-zero integers. The preferred odd integers for use in the present invention which provide harmonic frequencies that should be effective in alleviating post-stroke sequelae are selected from the group consisting of the following integers: three, five, seven, nine, eleven, thirteen, fifteen, seventeen and nineteen. Additional harmonic frequencies based on multiplying the fundamental frequency by an odd integer may also be suitable in some applications. As indicated, the frequencies for a given preselected ion and known magnetic flux density B can be determined with reference to the equation $f_{ch} = XBq/2\pi m$ where $f_{ch}$ is the frequency in Hertz of the fluctuating magnetic field along a predetermined axis extending through the target tissue, B is the magnetic flux density along the axis in Tesla, q is the charge of the preselected ion in Coulombs, m is the mass of the preselected ion in kilograms, and X is a selected odd integer greater than one. It is believed that many of the preferred odd multiple harmonic frequencies will be substantially as effective in alleviating post-stroke sequelae as are the fundamental frequencies.

In another aspect, the present invention provides a method for alleviating post-stroke sequelae which comprises generating an applied magnetic field parallel to a predetermined axis which projects through the designated space. In the presence of at least two different predetermined ionic species in the cerebral target tissue, the cerebral tissue is exposed to the applied magnetic field. In one embodiment, the tissue is also exposed to a local magnetic field having a component parallel to the predetermined axis. The magnetic flux density along the predetermined axis is fluctuated to create a non-zero average value. Where a local field is also present, this non-zero average value is the net non-zero average value of the applied and local field components parallel to the predetermined axis as previously described in connection with the other embodiments of the present invention.

A predetermined relationship between the frequency of the fluctuations and the non-zero average value of the magnetic flux density along the axis is then created and maintained which simultaneously controls the movement of two or more preselected ions. Ion movement is brought about to decrease post-stroke sequelae. In one embodiment, the predetermined relationship is determined by first solving the equation $f_c = Bq/2\pi m$ at a generally randomly selected value of B for each distinct preselected ion, where $f_c$ is the frequency of the field fluctuations in Hertz, B is the non-zero average value of the flux density parallel to the predetermined axis in Tesla, q is the charge of each preselected ion in Coulombs, and m is the mass of each preselected ion in kilograms. The value of B is preferably between about 1.0 and about 10,000 p Tesla. This establishes the fundamental cyclotron frequency for each ion. A value $f_{cs}$ is preferably selected such that none of the individual ion $f_c$ values deviate more than 5 percent from the $f_{cs}$ value. In most instances, there will be no $f_{cs}$ value available based on the fundamental $f_c$ values of the preselected ions. Accordingly, a higher odd harmonic frequency of at least one of the preselected ions is determined with the equation $f_{ch}=XBq/2\ \pi m$ as previously explained. The values of $f_c$ and $f_{ch}$ are examined to determine whether an $f_{ch}$ value can be selected based on a 10 percent and most preferably a 5 percent deviation factor. If not, the process is continued for each value of $f_{ch}$, beginning with the lowest odd harmonic $f_{ch}$ values until a value of $f_{cs}$ can be established within the 5 percent deviation. Hence, at the value selected for B during the calculation of the $f_c$ or $f_{ch}$ values, the magnetic flux density to which the target tissue is exposed is fluctuated along the axis at the $f_{cs}$ frequency. This specific relationship between frequency and field strength brings about simultaneous transmembrane movement of the preselected ions.

In more detail, the fundamental frequency at which the fluctuating magnetic field would be oscillated for cyclotron resonance regulation of transmembrane ion movement is calculated individually for each different ionic species to be regulated using the equation $f_c=Bq/2\ \pi m$ for a selected value of B, which is again the non-zero average value of the flux density along the predetermined axis. As previously explained, $f_c$ is in Hertz, q is in Coulombs, m is in kilograms, and q/m is the charge-to-mass ratio of the preselected ion. Once the fundamental cyclotron resonance frequency ($f_c$) of each ion to be regulated is calculated, a regulating frequency ($f_{cs}$) is determined which is preferably within 5 percent of the fundamental frequency $f_c$ or an odd harmonic frequency $f_{ch}$ of each preselected ion. The odd harmonic frequencies are determined again using the equation $f_{ch}=XBq/2\ \pi m$, where X is an odd integer greater than one. It will be understood that the equation $f_{ch}=XBq/2\ \pi m$ can be used to determine the fundamental frequency $f_c$ by using a value of 1 for X. While the value of $f_{cs}$ will not typically be available which is common to the fundamental frequencies and/or odd harmonic frequencies for each preselected ion, it has been found that an $f_{cs}$ value which is within about 10 percent and preferably about 5 percent of each $f_c$ value or $f_{ch}$ value of the ions to be regulated satisfactorily provides simultaneous transmembrane movement of each preselected ion in the field.

It will also be understood that the values of $f_{ch}$ are a function of B. Thus, it may be possible to obtain an $f_{cs}$ value for a particular set of ions which is within the preferred 5 percent deviation at a designated B value, but not a higher B value. For use in the present invention, the value of B is preferably between about 1.0 to about 10,000 p Tesla, with a peak-to-peak amplitude of about 2.0 to about 20,000 p Tesla. Again, the waveform is not critical. The preferred ions are those previous set forth.

The following example is provided to more fully illustrate the present invention and is not intended to limit the scope of the invention as defined in the appended claims.

EXAMPLE

The incorporation of isotopic $^{45}Ca$ in mixed human lymphocytes was measured following one-hour exposure of these cells to combined steady and periodic magnetic fields tuned to various cyclotron resonance conditions, including that corresponding to the charge-to-mass ratio for ionic $^{45}Ca$. Equal numbers of cells, prepared by dividing the original batch immediately prior to the above one-hour exposure, were not exposed during this one-hour period and therefore served as controls, subject only to the ambient magnetic field in the laboratory. The dc magnetic field was adjusted to $20.9\times10^{-6}$ Tesla at the exposure site. Just before dividing the cells into these exposed and control categories, radioactive $^{45}Ca$ was added to the medium in which the cells were suspended. Immediately following this one-hour period, the plates containing the experimental and control cells were centrifuged for five minutes, three cell washes performed, and the cells collected on filter paper for beta counting. Ratios of counts of exposed experimental cells to non-exposed control cells were obtained in triplicate for each exposure condition.

The ratios so obtained at three different magnetic field frequencies were

| $f_1$ frequency in Hertz | Ratio of $^{45}Ca$ activity, exposed cells to non-exposed cells ± standard deviation |
| --- | --- |
| 13.5 | 1.93 ± 0.27 |
| 14.3 | 3.14 ± 0.38 |
| 15.3 | 1.96 ± 0.51 |

This constitutes evidence that the one-hour exposure of these cells to the cyclotron resonance condition for isotopic $^{45}Ca$ resulted in a large transfer of $^{45}Ca$ into the cell, compared to other frequencies and compared to control (i.e., non-exposed) cells. The cyclotron resonance tuning frequency for $^{45}Ca$ is calculated from $$f_0 = \frac{1}{2\pi}\frac{q}{m}B_0$$

The charge-to-mass ratio (q/m) for $^{45}Ca$ equals $4.29\times10^6$ Coulombs/kilogram. Thus $$f_0 = \frac{1}{2\pi}\times 4.29\times 10^6 \times 20.9 \times 10^{-6} = 14.27\ \text{Hertz}$$

This calculated frequency is substantially the same as the frequency used in the data shown above, establishing the fact that a maximum transport of ions occurs under the magnetic exposure condition corresponding to the cyclotron resonance tuning condition.

What is claimed is:

1. A method for the therapeutic treatment of stroke victims, comprising:
   generating with a magnetic flux generator an applied magnetic flux parallel to an application axis and projecting through a stroke victim,
   said flux generator having at least two field coils, said field coils having a coil axis extending there through parallel to said application axis, each of said field coils further having at least two windings, one of said windings of each coil being an ac winding and the other of said windings being a dc winding, said ac winding having an associated full-wave rectifier and an oscillator;

measuring an ambient field existing along said application axis in the region of said stroke victim;

said applied magnetic flux generating step including the steps of generating with said dc winding a magnetic flux which reduces said ambient field to substantially zero and generating with said ac windings an ac magnetic field having a component along said application axis, said ac magnetic field component having an rms value which therapeutically treats post-stroke sequelae of said stroke victim by at least partially reducing ion imbalance in tissues affected by said stroke.

2. A method for the therapeutic treatment of stroke, comprising:

generating an applied magnetic field parallel to an axis projecting through a region of cerebral tissue of a stroke victim, said applied magnetic field resulting in a magnetic flux density of a known average value parallel to said axis, said cerebral tissue having been damaged during a stroke and exhibiting post stroke sequelae;

fluctuating said magnetic flux density such that said known average value is a non-zero average value;

creating a relationship between a frequency of said fluctuations and said non-zero average value of said magnetic flux density, wherein said relationship is a function of $f_{ch} = XBq/2\pi m$, where $f_{ch}$ is the frequency of the fluctuating magnetic flux density in Hertz, B is the non-zero average value of the flux density parallel to said axis in Tesla, q is the charge of an ion present in said cerebral tissue in Coulombs, m is the mass of said preselected ion in kilograms, and X is a selected odd integer greater than 1, such that said applied magnetic field is effective in therapeutically treating post-stroke sequelae of said stroke victim by at least partially reducing ion imbalance in tissues affected by said stroke.

3. The method recited in claim 2, further including subjecting said cerebral tissue to a local magnetic field having a component parallel to said axis and wherein said non-zero average value of said magnetic flux density is a net average value which includes the magnetic flux density of said component of said local magnetic field.

4. The method recited in claim 2, further comprising selecting said selected odd integer from the group consisting of odd integers from 1 to 19.

5. The method recited in claim 2, wherein said ion is selected from the group consisting of Li+, K+, Mg++ and Ca++.

6. a method for the therapeutic treatment of a stroke victim, comprising the steps of:

generating a fluctuating applied magnetic field parallel to an axis projecting through a space in which a region of cerebral tissue of a living subject is position, said applied magnetic field resulting in a magnetic flux density in said space of a known non-zero average value parallel to said axis;

fluctuating said magnetic flux density such that said known average value is a non-zero average value;

selecting at least two ions present in said cerebral tissue;

determining a value $f_{ch}$ for each of said selected ions where $f_{ch} = XBq/2\pi m$, and where B is said non-zero average value of said magnetic flux density along said axis, q is the charge of each of said ions in Coulombs, m is the mass of each of said ions in kilograms and X is a selected positive non-zero odd integer;

selecting a value $f_{cs}$ in Hertz from which each value $f_{ch}$ deviates less than a predetermined percentage;

fluctuating said magnetic field parallel to said axis at a rate which is equal to said $f_{cs}$ value; and maintaining the ratio of said $f_{cs}$ rate of fluctuation to said non-zero average value of said magnetic flux density parallel to said axis, whereby said $f_{ch}$ value and said ratio are effective in allowing said magnetic field to alleviate post-stroke sequelae in said cerebral tissue of said stroke victim by at least partially reducing ion imbalance in tissues affected by said stroke.

7. The method recited in claim 6, wherein said predetermined percentage is less than about 5 percent.

8. The invention recited in claim 6, wherein said at least two different selected ions comprises three ions.

9. The method recited in claim 10, wherein said selected odd integer is selected from the group consisting of 1, 3, 5, 7, 9, 11, 13, 15, 17 and 19.

10. The method recited in claim 6, wherein said selected ions are selected from the group consisting of Li+, K+, Mg++ and Ca++.

11. A method for the therapeutic treatment of a stroke victim comprising the steps of:

positioning a magnetic field generator adjacent a region of cerebral tissue in a living subject which has been damaged during a stroke such that said region of tissue occupies a treatment space;

generating a magnetic flux with said magnetic field generator, said magnetic flux extending through said region of cerebral tissue parallel to an axis projecting through said treatment space; and fluctuating said magnetic flux and controlling a density of said magnetic flux to create and maintain a relationship between a frequency of said fluctuations and the magnitude of said magnetic flux density wherein said magnetic flux therapeutically treats post-stroke sequelae in said victim by at least partially reducing ion imbalance in tissues affected by said stroke.

12. The method recited in claim 11, wherein said magnetic flux is combined with an ambient magnetic flux present in said region of cerebral tissue to create a composite magnetic flux density.

13. The method recited in claim 11, wherein said relationship of said frequency to said magnitude of said magnetic flux density is a function of $$f_c/B = q/(2\pi m)$$

where $f_c$ is said frequency in Hertz, B is the average value of said magnetic flux density in Tesla parallel to said axis, q/m has a value of from about $5 \times 10^5$ to about $100 \times 10^6$ in Coulombs per kilogram and where B preferably has a value not in excess of about $1 \times 10^{-2}$ Tesla.

14. The method recited in claim 13, wherein q and m are, respectively, equal to the charge and mass of a an ionic species present in said cerebral tissue.

15. The method recited in claim 14, wherein said preselected ionic species is selected from the group consisting of Li+, K+, Mg++ and Ca++.

* * * * *